United States Patent [19]

Borghi

[11] Patent Number: 5,938,695
[45] Date of Patent: Aug. 17, 1999

[54] CORONARY ENDOPROTHESIS SUCH AS A STENT

[75] Inventor: Enzo Borghi, Budrio, Italy

[73] Assignee: X-Trode, S.r.I, Italy

[21] Appl. No.: 08/669,329

[22] PCT Filed: Nov. 2, 1995

[86] PCT No.: PCT/IT95/00174

§ 371 Date: Jul. 3, 1996

§ 102(e) Date: Jul. 3, 1996

[87] PCT Pub. No.: WO96/14029

PCT Pub. Date: May 17, 1996

[30] Foreign Application Priority Data

Nov. 8, 1994 [IT] Italy ................................ BO94A0488

[51] Int. Cl.⁶ .................................................. A61F 2/06
[52] U.S. Cl. .................................................... 623/1
[58] Field of Search .................... 623/1, 12; 606/194, 606/195, 198

[56] References Cited

U.S. PATENT DOCUMENTS 5,354,308  10/1994  Simon et al. .

FOREIGN PATENT DOCUMENTS 0282175  9/1988  European Pat. Off. .
0312852  4/1989  European Pat. Off. .
0378151  7/1990  European Pat. Off. .
0461791  12/1991 European Pat. Off. .
0472731  3/1992  European Pat. Off. .
1199110  11/1959 France .

*Primary Examiner*—John G. Weiss
*Assistant Examiner*—John M. Black
*Attorney, Agent, or Firm*—Arthur Z. Bookstein; John F. Perullo

[57] ABSTRACT

The stent appears as a prismatic cage (3) of which the flat faces consist in a corresponding number of modular elements (2) linked one to the next in sequence, each comprising a pair of first mutually parallel tubular elements (4), fashioned in a biocompatible material, and a pair of filiform spacer elements (5), likewise biocompatible, which are inserted into the first tubular elements (4) in such a way that the assembled modular element (2) assumes a closed quadrangular configuration; each of the spacer elements (5) is deformable along its own longitudinal axis (X) so that the distance (D) separating the pair of first tubular elements (4) can be varied between a non-operative position of minimum clearance, in which the spacer elements (5) are collapsed and folded, and a stable operating position in which the first tubular elements (4) are spread fully apart with the spacer elements (5) at right angles to them.

26 Claims, 5 Drawing Sheets

CORONARY ENDOPROTHESIS SUCH AS A STENT

TECHNICAL FIELD

The present invention relates to a coronary endoprosthesis.

The art field of surgery currently embraces various types of coronary endoprostheses, referred to more familiarly as "stents" by those skilled in the art, designed for use in cases where a patient may be diagnosed as suffering from a vascular occlusion, in particular a blockage of the coronary arteries which have the important function of carrying blood to the cardiac muscle.

A stent consists generally in a tubular element of varying thickness and geometry that serves, when introduced by means of a catheter and expanded with an inflatable balloon, to establish a small duct matching the contours of the vessel into which it is inserted; the purpose of the endoprosthesis is therefore to keep the blood vessel open.

BACKGROUND ART

The field of biomedical engineering currently embraces a variety of endoprosthetic solutions: in a first such solution, disclosed in EP 461 791, the resulting stent takes the form of a small metallic tubular element of which the cylindrical surface is pierced by micro slots or cuts; when installed in a blood vessel, the tubular element is enlarged and deformed, permanently, in such a way that the slots are expanded to form diamond apertures and the tube is effectively transformed into a mesh duct.

In a second solution, disclosed in EP 282 175, the tubular element of the stent consists in a single metal wire formed initially into a flat serpentine appearing as a plurality of elongated loops with rectilinear members and interconnecting bends, and with no break in continuity; the flat element is compressed radially over the balloon catheter and inserted into the coronary vessel, then spread to the required dimensions by expanding the balloon, exploiting a "mechanical memory" incorporated into the selected wire material.

In other solutions, as disclosed in EP 312 852 and EP 378 151, use is made of single spiral wound metal wires, similarly implanted by means of a balloon catheter, of which the configuration and the diametral and axial dimensions can be varied likewise thanks to the "memory" of the particular metal selected.

"Memory" in this context signifies the facility whereby a material can be manipulated when exposed to particular mechanical, thermal or environmental conditions, to the end of bringing about a change in configuration; for example, in the case where a wire or mesh is made from an alloy of titanium and nickel, or from stainless steel or music wire, or from an annealed metal, change is induced by virtue of a mechanical memory, and in the case of certain materials such as the aforementioned titanium and nickel alloy, by virtue of a thermal memory.

It is known and scientifically proven that the successful manufacture of coronary endoprostheses guaranteeing both safety over time and operational efficiency is dependent on key requirements linked to mechanical and physiological factors: firstly, there is the need to ensure a sound resistance to radial deformation, given that the artery functions as a means of conveying blood under pressure and in consequence is subjected to a pressor action that the stent must be able to withstand; and secondly, there must be no effects generated that may upset the normal functioning of the artery.

In view of this second requirement, it is in fact inadvisable to fashion a stent exhibiting extensive surfaces fragmented by relative slots or openings; over time, these can create interstices favouring the build-up of atherosclerotic plaque, of which the physical impact is not inconsiderable. On the other hand, compact stents fashioned with extensive contact surfaces and more consistent thicknesses can lead to the risk of thrombosis.

It is therefore essential in manufacture to ensure a favourable balance between the surface area of the stent and the gauge of the metal utilized.

Accordingly, the object of the invention is to overcome the aforementioned drawbacks.

DISCLOSURE OF THE INVENTION

The stated object is realized, in accordance with the present invention, through the adoption of a coronary endoprosthesis structured in such a way as to optimize the balance between surface area and voids and thus procure full advantage in terms of mechanical properties, namely strength and ease of deformation, elastic and plastic alike, as well as of physical and chemical compatibility with the blood vessel and the bloodstream.

The invention will now be described in detail, by way of example, with the aid of the accompanying drawings, in which.

Figure 1:
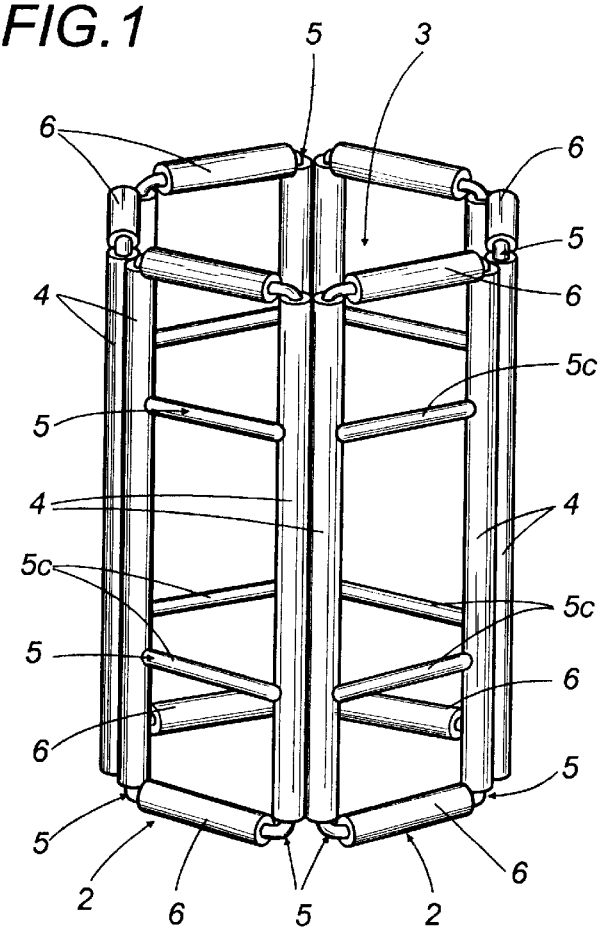
FIGS. 1 and 2 illustrate a coronary endoprosthesis in an expanded operating configuration, viewed in perspective and from one end, respectively.
Figure 3:
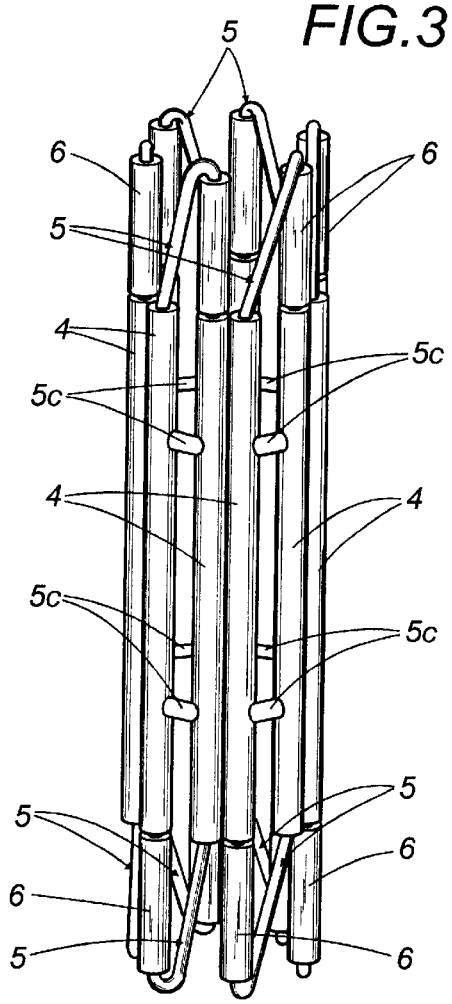
FIGS. 3 and 4 illustrate the endoprosthesis of FIGS. 1 and 2 in a contracted and non-operative configuration, viewed in perspective and from one end respectively.
Figure 2:
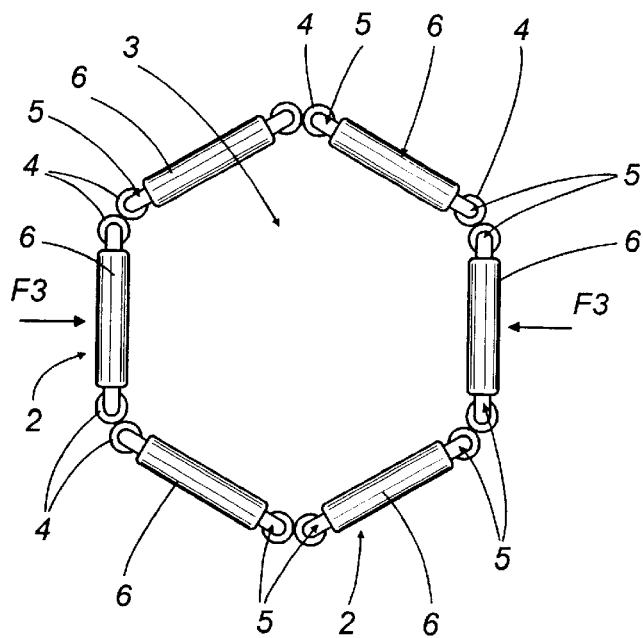
Figure 4:
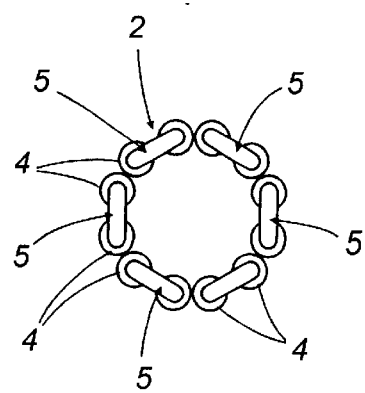
Figure 5:
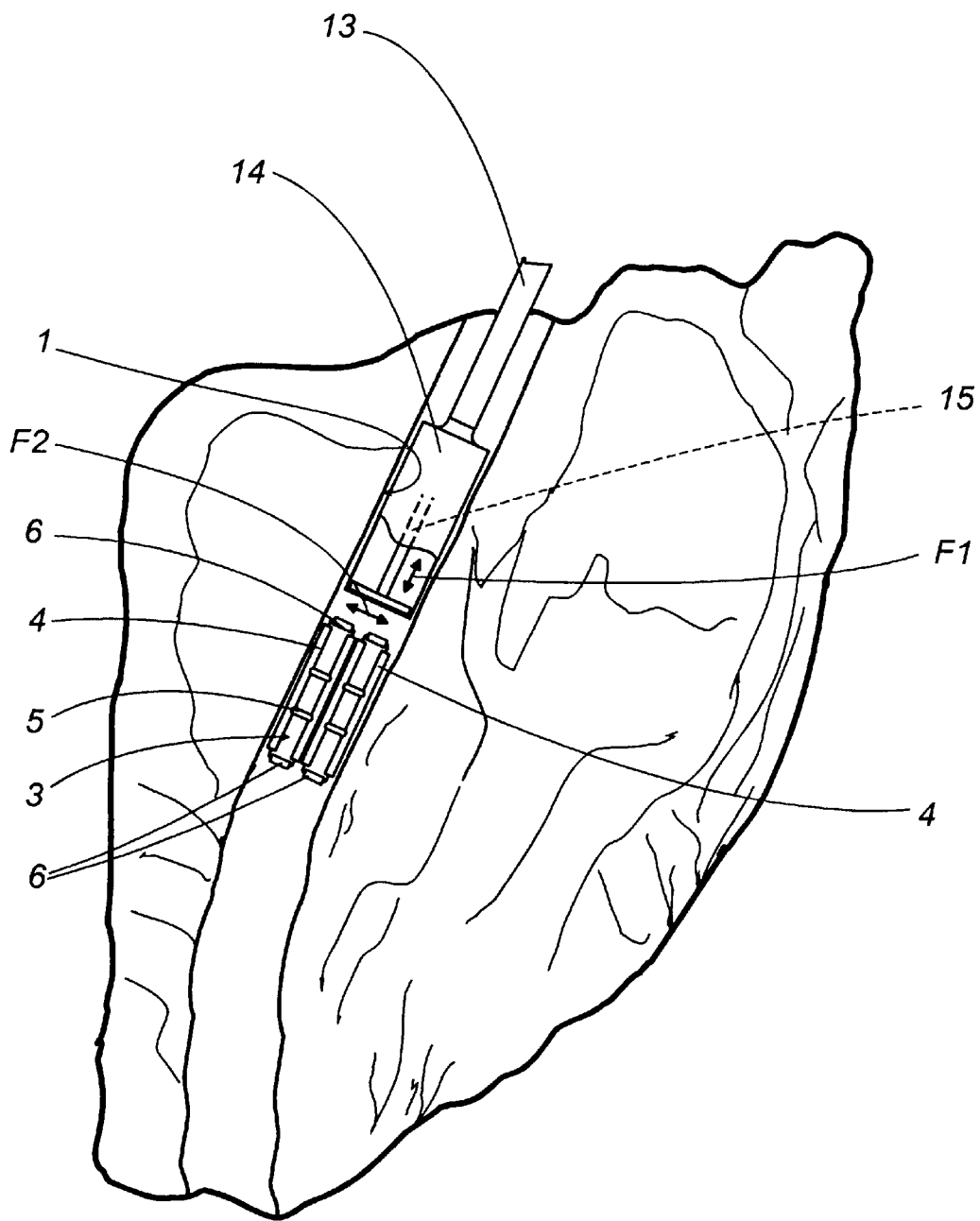
FIG. 5 illustrates the endoprosthesis of FIGS. 1 to 4 on a different scale, viewed during the process of implantation in a coronary cavity of a cardiac muscle.
Figure 6:
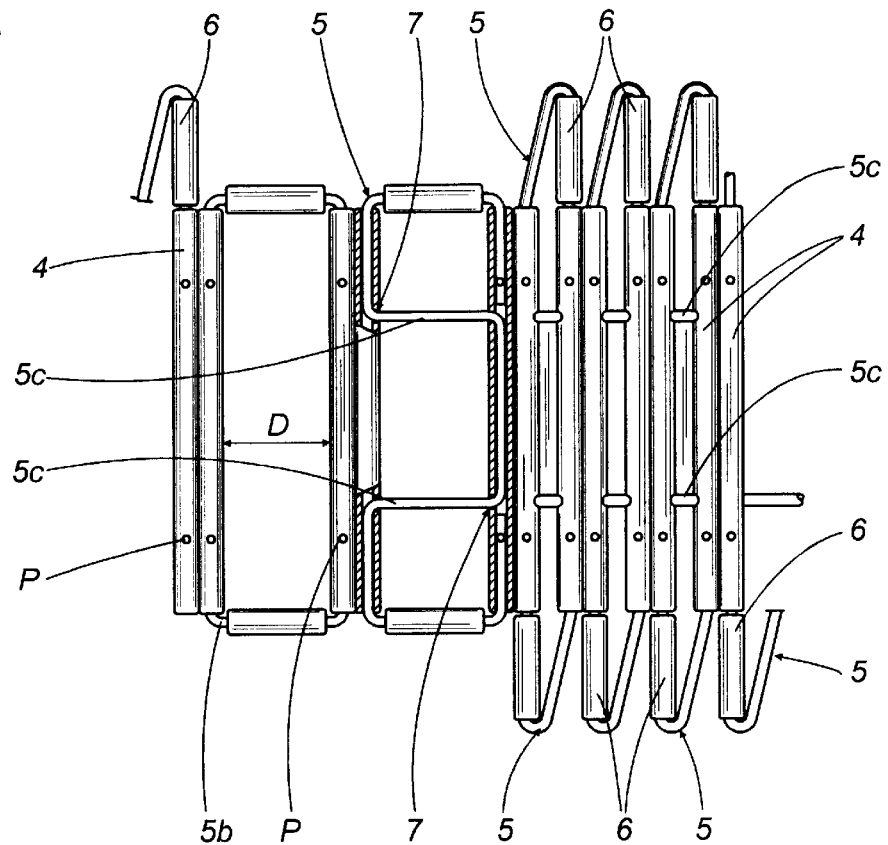
FIG. 6 illustrates the endoprosthesis of FIGS. 1 to 4 in a single part sectional and developed view showing the same two configurations, expanded and contracted.
Figure 7:
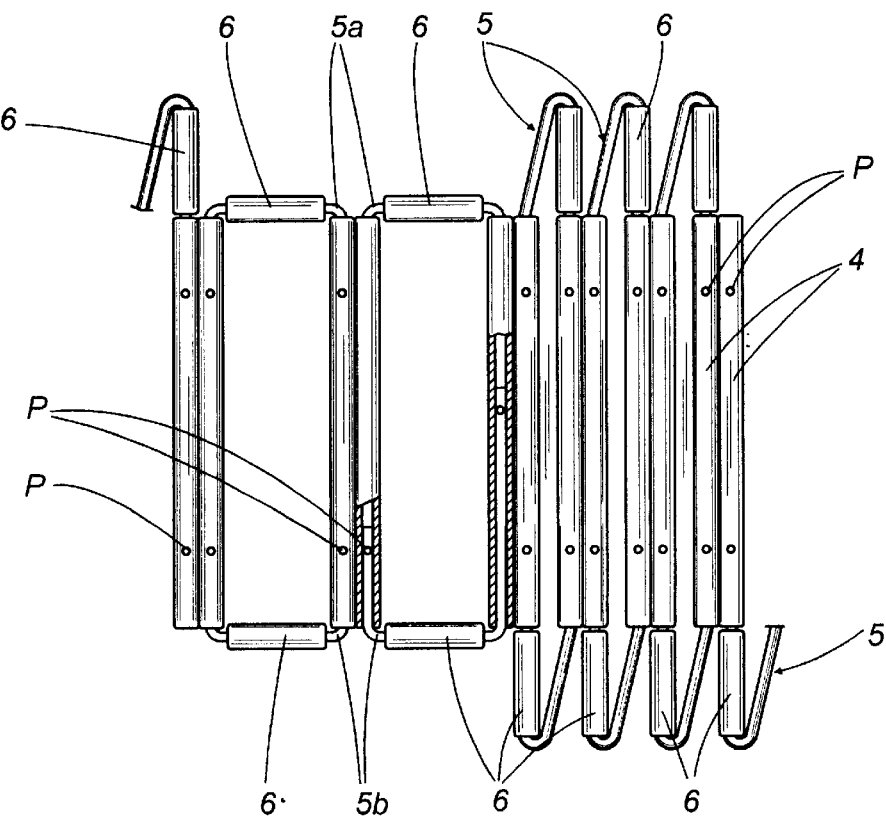
FIG. 7 illustrates an alternative embodiment of the endoprosthesis as in preceding drawings, seen in a single part sectional and developed view showing the same two configurations, expanded and contracted.

As discernible from the accompanying drawings, and referring first to FIGS. 1 to 5 in particular, the coronary endoprosthesis to which the invention relates, known as a stent, is utilized to maintain a regular flow of blood through parts of obstructed blood vessels 1, and especially cardiac arteries, in which the stent can be implanted.

The stent shown in FIGS. 1, 2, 3 and 4 comprises a plurality of modular elements 2 connected one to another in such a way as to form a tubular cage 3 of prismatic geometry, with one modular element 2 constituting each face of the prism; the single element 2 essentially comprises a pair of mutually parallel first tubular elements 4 fashioned from a biocompatible material, and a pair of filiform spacer elements 5, also in biocompatible material.

These two pairs of elements provide the basis on which to design and assemble a variety of stents differing structurally in terms both of geometry and of the physical properties possessed by the materials used in fabrication.

Observing the solutions illustrated in FIGS. 1–4 and FIGS. 6 and 7 only, each first tubular element 4 will be seen to consist in a tubular cylinder with a single central bore; in the case of the pair of spacer elements 5, on the other hand, a material of filiform embodiment is used in all of the solutions illustrated in the accompanying drawings.

The filiform spacer elements 5 are inserted in and associated with the first tubular elements 4 in such a manner that the modular element 2 assumes a closed quadrangular shape of reducible proportions: this particular characteristic is attributable to the spacer elements 5, which are deformable along their longitudinal axis X (the definition applies even for a non rectilinear axis, in the event that the filiform material should present a shape other than cylindrical) so as to allow a variation in the distance D separating the first tubular elements 4 from a position of minimum clearance, in which the selfsame two elements 4 are substantially in mutual contact (as discernible clearly in FIGS. 3, 4 and 9) and the spacer elements 5 appear folded or looped, to a stable operating position of maximum clearance between the first tubular elements 4 (see FIGS. 1, 2 and 8), in which the spacer elements 5 are disposed at right angles to the first tubular elements 4. Each single module 2 is thus deformable within its respective plane, so that the resulting prismatic structure, in short, the endoprosthetic structure to which the invention relates, is rendered capable of contraction or expansion in the radial direction (see in particular FIGS. 1 to 4).

In practice each modular element 2 is fashioned from a pair of first tubular elements 4 and one or two spacer elements 5, and the assembled modular elements 2 are anchored together by means of a weld (preferably using laser equipment) effected between the respective first tubular elements 4 disposed in mutual contact.

Figure 8:
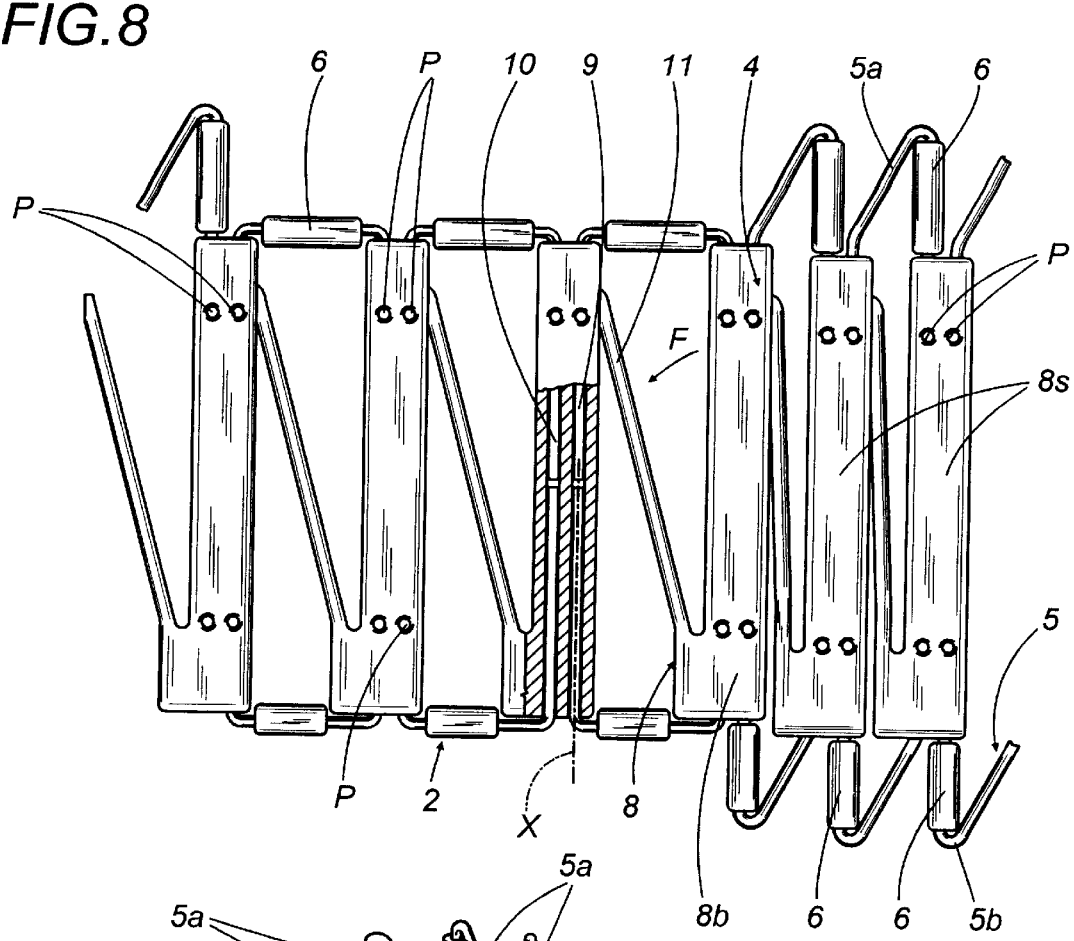
FIGS. 8 and 9 illustrate a further variation in embodiment of the endoprosthesis of the preceding drawings, seen respectively in a part sectional and developed view showing both of the two expanded and contracted configurations, and in a perspective view showing the contracted configuration.
Figure 9:
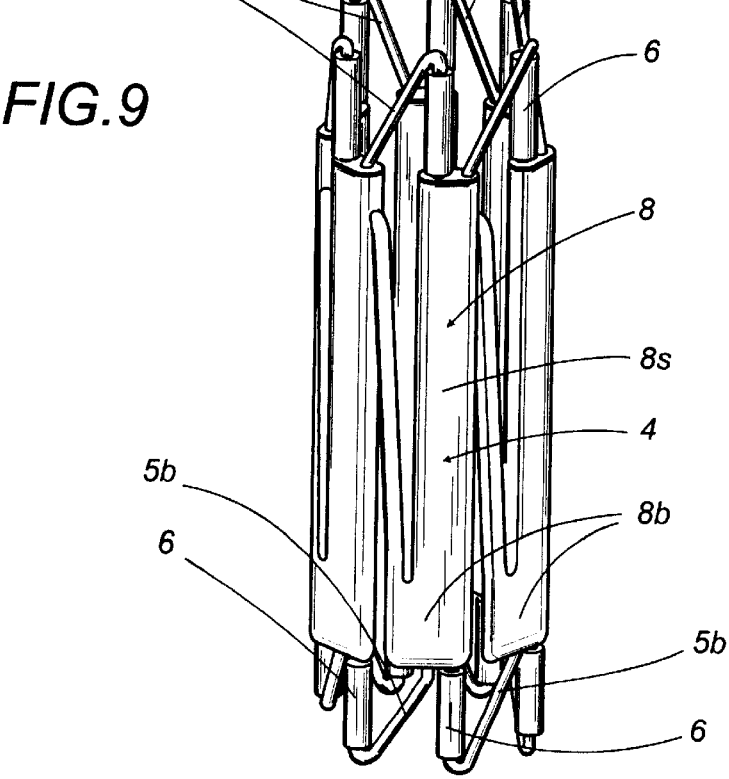

In the alternative embodiment shown in FIGS. 8 and 9, each first tubular element 4 consists in a solid member 8 of flat elongated section affording a pair of mutually parallel longitudinal bores 9 and 10 which pass through from end to end. Lodged internally of each bore 9 and 10 are two portions of respective mutually opposed spacer elements 5, each such portion inserted from a corresponding end of the relative bore 9 and 10: more exactly, the one bore 9 accommodates a pair of spacer elements 5 associated also with a preceding solid member 8 (that on the right as viewed in FIG. 8), whereas the other bore 10 accommodates a further pair of spacer elements 5 associated also with a successive solid member 8 (consequently, a pair of spacer elements 5 interconnects each modular element 2 with the next in sequence). In this solution, accordingly, the anchorage between consecutive modular elements 2 is provided by the selfsame spacer elements 5, as it is these that connect each two successive separate first tubular elements 4.

Each solid member 8 exhibits a base portion 8b of section fuller than the remaining stem 8s of the member, also an arm 11 extending from and embodied integrally with the lateral appendage afforded by the base portion 8b. The arm 11 extends at an angle in relation to the longitudinal dimension of the solid member 8 and is deformable elastically or plastically from an at-rest configuration (shown in FIG. 9 and the right hand part of FIG. 8), in which the arm 11 is positioned in close proximity to the stem 8s, and an operating configuration (left hand part of FIG. 8) in which the arm 11 is distanced from the stem 8s (see also arrow F), occupying a substantially diagonal position within the modular element 2 and with the free end bearing against the relative stem 8s of the successive solid member 8: thus, the aforementioned maximum clearance between the first tubular elements 4 is suitably obtained.

Figure 10:
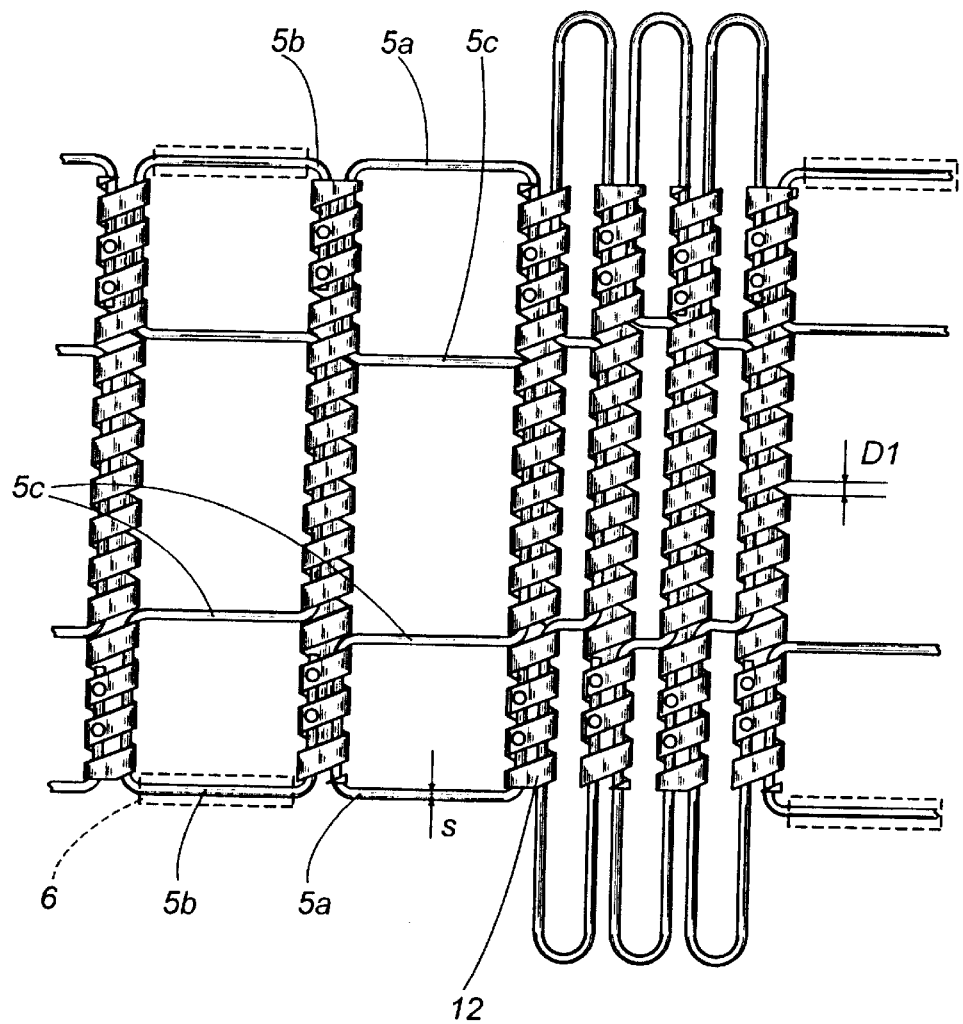
FIG. 10 illustrates another alternative embodiment of the endoprosthesis as in previous drawings, seen in a developed view showing two configurations, expanded and contracted.
Figure 11:
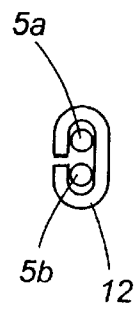
FIGS. 11 and 12 illustrate two details of a spiral wound element forming a part of the endoprosthesis of FIG. 10, seen respectively from one end and in a part sectional side elevation.
Figure 12:
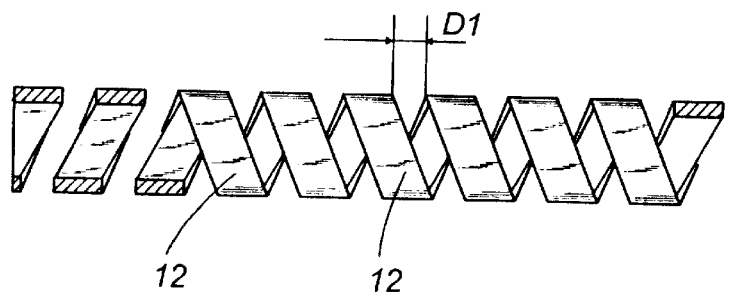

FIGS. 10, 11, 12 illustrate a further embodiment of the first tubular elements 4 in which each first tubular element 4 is embodied as a spiral wound member 12 of flat section exhibiting a distance D1 between single successive coils greater than the thickness S of the filiform spacer element 5, in such a way that the spacer element 5 is able to slide transversely in relation to the coils during the operation of expanding the modular elements 2. As discernible from FIGS. 10 and 11, each spiral wound member 12 slidably accommodates two portions of two distinct spacer elements 5 associated with a preceding spiral wound member 12 and a successive spiral wound member 12, respectively.

Examining the structure of the spacer elements in more detail, it will be observed that in certain solutions (see FIGS. 1–4 and FIG. 6) these consist in a single filiform element 5 slidably accommodated within each of the first tubular elements 4, whilst in other solutions, each first tubular element 4 accommodates two separate spacer elements 5a and 5b each inserted slidably at one end into a relative end of a first tubular element and bent to a "U" shape. In both types of solution (one or two spacer elements per module), the remaining free ends of the spacer elements 5 are restrained by means of punched indentations P applied externally to the relative ensheathing first tubular elements 4; the freedom of each spacer element 5 to move along its axis X internally of the respective first tubular element 4 is indispensable to the end of inducing the changes in configuration referred to above (see FIGS. 1 to 4 and 6 and 7).

The filiform spacer elements 5 are fashioned preferably from a biocompatible material having physical properties different from those of the material adopted for the first tubular elements 4 in such a way as to be deformable with ease when subjected to physical and/or environmental changes (i.e. mechanical or thermal, plastic or elastic according to the applied force of deformation or to the material utilized, as will become clear in due course).

As discernible in all solutions illustrated, the modular element 2 may further comprise rigid second tubular elements 6, coaxially ensheathing portions of the filiform spacer elements 5 located externally of the pair of first tubular elements 4 and fashioned likewise in a biocompatible material, though with physical properties different to those of the filiform material: the purpose of the second tubular element 6 is to function as a strut capable of counteracting radial compression forces, thereby stiffening the structure of the spacer element 5 externally of the first tubular elements 4 and thus rendering the entire modular element 2 more stable when fully expanded.

As already intimated, each modular element 2 in the example of FIGS. 1 to 4 and FIG. 6 comprises a single filiform spacer element 5 of which the free ends are inserted into one first tubular element 4 of the pair. The remaining length of the filiform material between the free ends is threaded through relative radial holes 7 afforded by the selfsame first tubular elements 4 and passed back and forth in alternation between the two, thereby creating a plurality of intermediate transverse portions 5c and establishing a lattice structure within the quadrangular compass of the modular element 2, of which the effect is to make the latter mechanically more secure.

To obtain this variety of constructional types, the first tubular elements 4 can be fashioned from titanium, or stainless steel, or platinum, or even from an alloy of gold, according to the particular mechanical requirements (i.e. superior resistance to radial deformation within the blood vessel 1) and to the type of embodiment ultimately adopted: in the case of the solution with the flat solid member 8, for example, it is preferable to utilize a material also possessing good elastic or plastic deformability so that the arm 11 will spread in a suitably reliable manner when the stent is secured inside the blood vessel 1.

Similarly, the filiform spacer elements 5 can be fashioned in different materials to the end both of obtaining different types of deformation and of optimizing compatibility with the material selected for the first tubular elements 4: in a preferred solution, the material utilized for the spacer elements 5 might be an alloy of annealed platinum and iridium, or of annealed gold, or music wire (for mechanical type deformations) or a titanium and nickel alloy (for thermal type deformations).

Variations are possible likewise in the case of the material adopted for the aforementioned second tubular element 6, which preferably will be of the same type as for the first tubular element 4, i.e. stainless steel, titanium, platinum or gold alloy, so that greater mechanical strength can also be secured when appropriate on the shorter sides of the quadrangle compassed by the modular element 2.

The resulting stent can be implanted internally of the blood vessel in various ways, according to the type of material from which the spacer elements 5 are fashioned: where the spacer elements 5 are in music wire, for example (deformation by mechanical memory), the stent is inserted into the artery of the patient by means of a catheter 13 (conventional in embodiment and therefore illustrated only in part) and a hollow barrel 14 (see FIG. 5); the stent is in fact accommodated internally of the barrel 14 in a compacted, non-operative configuration (i.e. compressed radially as indicated by the arrow F3 of FIG. 2), and the barrel 14 connected to the distal extremity of the catheter 13. Before implantation, the blood vessel 1 is dilated so as to break up the plaque and roughen the wall of the lumen, thereby facilitating the contact between stent and wall.

At this point the catheter 13 is inserted into the vessel 1 with barrel 14 and stent 3 attached, and once the area of the occlusion is located, the stent 3 will be released. The barrel 14 opens in such a way that the stent 3 can be ejected by means of a plunger 15 (see arrow F1 in FIG. 5) extending through the catheter 13 and operated from outside the body, whereupon the modular elements 2 assume an expanded operating configuration that brings the endoprosthetic structure to its maximum diametral dimensions (see arrow F2, FIG. 5), exploiting the combined length of the various external portions of the spacer elements 5 and their mechanical elastic "memory"; the expansion of the stent internally of the lumen is thus brought about by virtue of the intrinsic elasticity of the material from which the spacer elements 5 are fashioned. Once the stent 3 has expanded to its final operating configuration internally of the blood vessel 1, the catheter 13 and the empty barrel 14 are withdrawn.

Conversely, in the case of a stent 3 assembled with spacer elements 5 incorporating plastic memory (so that the modular elements hold a configuration assumed after being extended radially by plastic deformation), the barrel 14 can be replaced by a balloon (not illustrated), or, in the event that the spacer elements 5 are fashioned from a material having thermal memory, by a distal probe similar to the balloon though in this instance equipped with a heater, over which the stent is positioned in the contracted configuration: the inserted probe can be piloted by way of the catheter to produce a change in temperature, whereupon the stent spreads to its operating configuration as a result of the thermal expansion induced.

The endoprosthetic structure disclosed offers a variety of constructional solutions compassing many of the implant situations typically encountered by surgeons, an advantage attributable above all to the modular configuration and to the adoption of different metals for the tubular elements and the spacer elements.

With a modular architecture, in effect, it is possible to vary the specifications of the stent even during manufacture: the diametral dimensions can be altered according to the size of the lumen, and there is also flexibility in length given that a plurality of prismatic cages can be connected in series and adapted thus to the natural shape of the blood vessel. Exploiting the diversity of suitable metals, moreover, different types of mechanical and physiological response can be obtained according to the position of the implant, and a proper balance struck in terms of the ratio between the volume of material incorporated (suitably minimized, and with rounded edges) and the size of the exposed surfaces (likewise minimized), so that there is neither any increased risk of thrombosis within the passage, thanks to a smooth flow of blood, nor any increase in the production of atherosclerotic plaque at the site of the implant.

In any event, the coronary endoprosthetic structure described and illustrated is eminently suitable for implantation in many types of blood vessel within the human body.

I claim:

1. A coronary endoprosthesis implantable in blood vessels, appearing as a tubular cage of prismatic geometry consisting of a plurality of modular elements connected one to another, each comprising:

a pair of first tubular elements formed from a biocompatible material and disposed parallel to one another;

a pair of filiform spacer elements, formed from a biocompatible material and associated with the first tubular elements in such a way that the assembled modular element exhibits a closed quadrangular configuration;

wherein the spacer elements are deformable each along a relative longitudinal axis with a result that a distance separating the first tubular elements can be varied by maneuvering the first tubular elements between a position of minimum clearance and substantially of mutual contact, in which the spacer elements exhibit a looped appearance, and a stable operating position of maximum clearance in which the spacer elements are disposed at right angles to the first tubular elements.

2. The coronary endoprosthesis of claim 1, wherein the pair of spacer elements consists of a single filiform element having a pair of free ends inserted slidably through each of the first tubular elements and restrained at the free ends by means of punched indentations applied externally to the first tubular element.

3. The coronary endoprosthesis of claim 1, wherein the pair of spacer elements consists of two single filiform elements each having a pair of free ends and each inserted slidably into corresponding ends of the pair of first tubular elements such that each exhibits the appearance of a letter "U", and restrained at their free ends internally of the respective first tubular elements by means of punched indentations applied externally to the tubular elements.

4. The coronary endoprosthesis of claim 1, wherein the spacer elements are formed from a material with physical properties dissimilar to those of the material from which the first tubular elements are formed.

5. The coronary endoprosthesis of claim 1, wherein the spacer elements are plastically deformable when subjected to mechanical force.

6. The coronary endoprosthesis of claim 1, wherein each of the spacer elements is associated with a second tubular element of rigid structure, apart from the pair of first tubular elements, formed from a biocompatible material and coaxially ensheathing the spacer element in such a way as to create an element by which the modular element is stiffened when in the stable operating position of maximum clearance.

7. The coronary endoprosthesis of claim 1, wherein each of the spacer elements is associated with a second tubular element of rigid structure, apart from the pair of first tubular elements, formed from a biocompatible material having physical properties different to those of the spacer element, and coaxially ensheathing the spacer element in such a way as to create an element by which the modular element is stiffened when in the stable operating position of maximum clearance.

8. The coronary endoprosthesis of claim 1 wherein each pair of the spacer elements consists of a single filiform element having a defined length and a pair of free ends, both of which occupy the same first tubular element with the length distributed between the two first tubular elements of the pair, passing through relative radial holes in the tubular elements and extending back and forth alternately to create a plurality of intermediate transverse portions, forming a lattice structure within the quadrangular compass of each modular element.

9. The coronary endoprosthesis of claim 1, wherein each first tubular element appears as a tubular cylinder with a central bore.

10. The coronary endoprosthesis of claim 1, wherein each first tubular element consists of a solid member of substantially flat section having, internally, a pair of mutually parallel through bores having open ends which are receptive to relative portions of paired spacer elements, one of said bores accommodating a pair of spacer elements associated with a preceding modular element and the remaining bore accommodating a pair of spacer elements associated with a successive modular element; and the solid member having externally, a base portion and a main stem portion, the base portion appearing broader in section than the main stem of the solid member and supporting an arm formed integrally at one end with a projection on the base portion, the other end of the arm being free and the arm being substantially divergent from the stem, and deformable in such a way that the solid member can be contracted from an operating configuration in which the arm is distanced from the stem and extends diagonally across the modular element with the free end bearing directly against the stem of a successive solid member, to an at-rest configuration in which the arm and stem of the solid member are substantially in mutual contract and the first tubular elements assume the position of minimum clearance.

11. The coronary endoprosthesis of claim 1, wherein each first tubular element consists of a spiral wound element of which the minimum distance between successive coils is greater than the thickness of the filiform spacer element, and the spiral wound element defining a bore that slidably accommodates two portions of two distinct spacer elements associated with corresponding adjacent modular elements.

12. The coronary endoprosthesis of claim 11, wherein the spiral wound element has a substantially flat section.

13. The coronary endoprosthesis of claim 1, wherein each modular element is anchored to a preceding and a successive element in sequence by welding the adjoining first tubular elements one to another.

14. The coronary endoprosthesis of claim 1, wherein the first tubular elements are formed from titanium.

15. The coronary endoprosthesis of claim 1, wherein the first tubular elements are formed from stainless steel.

16. The coronary endoprosthesis of claim 1, wherein the first tubular elements are formed from platinum.

17. The coronary endoprosthesis of claim 1, wherein the first tubular elements are formed from an alloy of gold.

18. The coronary endoprosthesis of claim 1, wherein the first spacer elements are formed from an alloy of annealed platinum and iridium.

19. The coronary endoprosthesis of claim 1, wherein the first spacer elements are formed from an alloy of annealed gold.

20. The coronary endoprosthesis of claim 1, wherein the first spacer elements are formed from music wire.

21. The coronary endoprosthesis of claim 1, wherein the first spacer elements are formed from an alloy of titanium and nickel.

22. The coronary endoprosthesis of claim 6, wherein the second tubular elements are formed from titanium.

23. The coronary endoprosthesis of claim 6, wherein the second tubular elements are formed from stainless steel.

24. The coronary endoprosthesis of claim 6, wherein the second tubular elements are formed from platinum.

25. The coronary endoprosthesis of claim 6, wherein the second tubular elements are formed from an alloy of gold.

26. The coronary endoprosthesis of claim 1, wherein the spacer elements are plastically deformable when subjected to a change in thermal environment.

* * * * *